United States Patent
Chirila et al.

(10) Patent No.: US 10,317,396 B2
(45) Date of Patent: Jun. 11, 2019

(54) PERIPHERAL DIAGNOSTIC METHODS FOR SCREENING ALZHEIMER'S DISEASE USING BETA AMYLOID AND INTERCELLULAR COMMUNICATION

(75) Inventors: Florin V. Chirila, Morgantown, WV (US); Tapan Kumar Khan, Morgantown, WV (US); Daniel L. Alkon, Bethesda, MD (US)

(73) Assignee: West Virginia University, Morgantown, WV (US)

( * ) Notice: Subject to any disclaimer, the term of this patent is extended or adjusted under 35 U.S.C. 154(b) by 226 days.

(21) Appl. No.: 14/116,138

(22) PCT Filed: May 11, 2012

(86) PCT No.: PCT/US2012/037532
§ 371 (c)(1),
(2), (4) Date: Apr. 14, 2014

(87) PCT Pub. No.: WO2012/155051
PCT Pub. Date: Nov. 15, 2012

(65) Prior Publication Data
US 2014/0248648 A1   Sep. 4, 2014

Related U.S. Application Data

(60) Provisional application No. 61/485,256, filed on May 12, 2011.

(51) Int. Cl.
*G01N 33/50* (2006.01)

(52) U.S. Cl.
CPC . *G01N 33/5091* (2013.01); *G01N 2800/2821* (2013.01)

(58) Field of Classification Search
CPC ............... G01N 33/5091; G01N 2800/2821
USPC ....................................................... 435/29
See application file for complete search history.

(56) References Cited

U.S. PATENT DOCUMENTS

2009/0029873 A1   1/2009   Khan
2011/0256565 A1*  10/2011  Schon ................ G01N 33/6896
                                                       435/11

FOREIGN PATENT DOCUMENTS

WO   WO 2011/041761 A1   4/2011

OTHER PUBLICATIONS

Khan et al. (2006). An internally controlled peripheral biomarker for Alzheimer's disease: Erk1 and Erk2 responses to the inflammatory signal bradykinin. PNAS, v103(35), p. 13203-13207.*
Etcheberrigaray et al. (1994). Soluble f-Amyloid Induction of Alzheimer's Phenotype for Human Fibroblast K+ Channels. Science, v264, p. 276-278.*
Cornforth et al. (2008). Automated classification reveals morphological factors associated with dementia. Applied Soft Computing, v8, 182-190.*
Rajput et al. (1993). Alzheimer's Disease and Idiopathic Parkinson's Disease Coexistence. J Geriatr Psychiatry Neurol, v6(3), p. 170-176.*
Squitieri (epub 2009). Abnormal morphology of peripheral cell tissues from patients with Huntington disease. J Neural Transm, v117(1), p. 77-73.*
Pani (2009). Altered Cholesterol Ester Cycle in Skin Fibroblasts from Patients with Alzheimer's Disease. Journal of Alzheimer's Disease, v18, p. 829-841.*
Chirla, F.V. et al., "Patterns of fibroblast networks screen for Alzheimer's disease", Society for Neuroscience Abstract Viewer and Itinerary Planner, vol. 40, 2010, Neuroscience Meeting of Society for Neuroscience, San Diego, CA.
International Search Report and Written Opinion for PCT/US2012/037532 dated Jul. 6, 2012 (11 pages total).
Aisen, Paul S. et al., "The Development of Anti-Amyloid Therapy for Alzheimer's Disease", CNS Drugs 2005, pp. 989-996.
Albert, Réka et al., "Brief Communications: Diameter of the World-Wide Web", Nature, Sep. 9, 1999, vol. 401.
Albert, Reka et al., "Statistical mechanics of complex networks", Reviews of Modern Physics, vol. 74, Jan. 30, 2002.
Ansel, John C. et al., "Progress in Derm", vol. 106, (1996) pp. 198-204.
Bellucci, Catia et al., "Differences in Extracellular Matrix Production and Basic Fibroblast Growth Factor Response in Skin Fibroblasts from Sporadic and Familial Alzheimer's Disease", Mol Med 13 (9-10), pp. 542-550, Sep.-Oct. 2007.
Chirila, Florin V. et al., "Development of gerbil medial superior olive: integration of temporally delayed excitation and inhibition at physiological temperature", J Physiol, 2007, pp. 167-190.
Citron, Martin et al., "Excessive production of amyloid β-protein by peripheral cells of symptomatic and presymptomatic patients carrying the Swedish familial Alzheimer disease mutation", Proc. Natl. Acad. Sci. USA vol. 91 pp. 11993-11997, Dec. 1994.
Endres, Kristina et al., "Upregulatoin of the x-secretase ADAM10—risk or reason for hope?", FEBS Journal 277 (2010) pp. 1585-1596.
Etcheberrigaray, Rene et al., "Therapeutic effects of PKC activators in Alzheimer's disease transgenic mice", PNAS Jul. 27, 2004, vol. 101, No. 30 pp. 11141-11146.
Fowler, James H. et al., "Dynamic spread of happiness in a large social network: longitudinal analysis over 20 years in the Framingham Heart Study", BMJ 2008, pp. 1-9.
Geyfman, Mikhail et al., "How the Skin Can Tell Time", Journal of Investigative Dermatology (2009), 129 pp. 1063-1066.
Hardy, John et al., "The Amyloid Hypothesis of Alzheimer's Disease: Progress and Problems on the Road to Therapeutics", Science 297, 353, Apr. 10, 2009.
Johnston, Janet A. et al., "Increase B-amyloid release and levels of amyloid precursor protein (APP) in fibroblast cell lines from family members with the Swedish Alzheimer's disease APP670/671 mutataion", FEBS Letters 354 (1994) pp. 274-278.
Khan, Tapan K. et al., "A cellular model of Alzheimer's disease therapeutic efficacy: PKC activation reverses AB-induced biomarker abnormality on cultured fibroblasts", Neurobiology of Disease 34 (2009) pp. 332-339.

(Continued)

*Primary Examiner* — Sean C. Barron
(74) *Attorney, Agent, or Firm* — Finnegan, Henderson, Farabow, Garrett & Dunner, LLP (57) ABSTRACT

The present disclosure relates to a peripheral diagnostic method for screening Alzheimer's disease in patients based on quantitatively measured complexity of skin-sampled fibroblast networks.

8 Claims, 8 Drawing Sheets

(56) References Cited

OTHER PUBLICATIONS

Kozikowski, Alan P. et al., "Searching for Disease Modifiers—PKC Activation and HDAC Inhibition—A Dual Drug Approach to Alzheimer's Disease that Reduces AB Production while Blocking Oxidative Stress", ChemMedChem Jul. 6, 2009 4(7), pp. 1095-1105.
Nagasaka, Yosuke et al., "A unique gene expression signature discriminates familial Alzheimer's disease mutation carriers from their wild-type siblings", PNAS Oct. 11, 2005 vol. 102, No. 41, pp. 4854-4849.
Repetto, Emanuel et al., "Presenilin 1 Regulates Epidermal Growth Factor Receptor Turnover and Signaling in the Endosomal-Lysosomal Pathway", J. Biol. Chem., vol. 282, No. 43, pp. 31504-31516.
Schreml, Stephan et al., "Amyloid in skin nd brain: What's the link?", John Wiley & Sons A/S, Experimental Dermatology, 19, (2010), pp. 953-957.
Selkoe, Dennis J. et al., "Alzheimer's disease results from the cerebral accumulation and cytotoxicity of amyloid B-protein", Journal of Alzheimer's Disease 3 (2001), pp. 75-80.
Strogatz, Steven H. et al., "Exploring complex networks", Nature, vol. 410, Mar. 8, 2001, p. 268.
Tanioka, Miki et al., "Molecular Clocks in Mouse Skin", Journal of Investigative Dermatology (2009) 129, pp. 1225-1231.
Tournoy, Jos et al., "Partial loss of presenilins causes seborrheic keratosis and autoimmune disease in mice", Human Molecular Genetics, vol. 13, No. 13, pp. 1321-1331.
Vierbuchen, Thomas et al., "Direct conversion of fibroblasts to functional neurons by defined factors", Nature, vol. 463, Feb. 25, 2010, pp. 1035-1038.
Watts, Duncan J. et al., "Collective dynamics of 'small-world' networks", Nature, vol. 393, Jun. 4, 1998.

* cited by examiner

PERIPHERAL DIAGNOSTIC METHODS FOR SCREENING ALZHEIMER'S DISEASE USING BETA AMYLOID AND INTERCELLULAR COMMUNICATION

This application claims the benefit of U.S. provisional Application No. 61/485,256, filed on May 12, 2011, the entirety of which is incorporated herein by reference.

The present disclosure relates to peripheral diagnostic methods for screening Alzheimer's disease in patients based on quantitatively measured complexity of skin-sampled fibroblast networks.

Alzheimer's disease (AD) is a neurodegenerative disorder characterized by the progressive decline of memory and cognitive functions. It is estimated that over five million Americans are living with this progressive and fatal disease. Alzheimer's disease destroys brain cells, causing memory loss and problems with thinking and behavior that decrease quality of life. While AD has no known cure, treatments for symptoms can improve the quality of life of the millions of people suffering from AD, and that of their families. An early diagnosis of AD gives the patient time to make choices that maximize quality of life and to plan for the future, reduces anxiety about unknown problems, and provides a better chance for the patient benefiting from treatment.

The complexity of AD raises a great challenge for early screening. A biological marker that would predict AD prior to symptomatic diagnosis or definitively diagnose early AD could have a major impact in testing and treating AD. The long term prodromal stages, co-morbidity with other non-Alzheimer's disease dementia (non-ADD) and multi-factorial nature of AD offer further challenges for successful diagnosis.

Thus, there exists a need in the art for improved methods of diagnosing Alzheimer's disease.

BRIEF DESCRIPTION OF THE DRAWINGS

FIG. 2E shows population data for the integrated score for skin fibroblasts at 48 hours. FIG. 2F plots the integrated score for AD cells as a function of disease duration in years. The numbers beneath each point represent the number of cell lines, and error bars represent the standard error of the mean.

FIGS. 3A and 3B show AD and AC fibroblast cells, respectively, 48 hours after plating in Matrigel. FIG. 3C shows Area/# population data for AC (n=11), AD (n=13), and non-ADD (n=9). FIG. 3D shows the Area/# as a function of disease duration in years. The numbers beneath each point represent the number of cell lines, and error-bars represent the standard error of the mean. FIGS. 3E and 3F show two views of the same probability distribution of cellular aggregates as a function of area and number 48 hours after plating.

FIG. 4A shows repeatability of results for AC (n=1), AD (n=1), and non-ADD (n=2); experiments were done at least one month apart for the same cell lines, and the initial number of cells was within 10%. FIG. 4B plots the area per number of aggregates as a function of initial cell density, showing an exponential relationship (solid lines) with a steeper rise for AD than for AC. Error bars represent the standard deviation. The fit function is $f(x)=a*exp(x/b)$ where $a=112.8$ and $b=22.8$ for AD and $a=64.1$ and $b=30.5$ for AC. This suggests that for a cell density of 50 cells/mm$^3$ the separation is reasonably good for screening AD.

FIG. 5A shows AC cells 1 hour after plating in Matrigel (fractal dimension=1.72, lacunarity=0.37), and FIG. 5B shows the same cells 48 hours after plating (fractal dimension=1.05, lacunarity=0.75). FIG. 5C shows fractal curves for AD, AC, and non-ADD cells, wherein the recovery slope and intercept were monitored by fitting a line (pink) in the range 20-80% of the max-min difference. FIG. 5D shows population data for slope versus intercept of the recovery for fractal curves AD (n=13), AC (n=10), and non-ADD (n=9) shown in FIG. 5C. FIG. 5E shows lacunarity curves for AD, AC, and non-ADD cells, and FIG. 5F shows the average lacunarity as means for separating the three groups (AD (n=7), AC (n=6), non-ADD (n=8)).

FIG. 6 illustrates cell migrating analysis. Examples of freely migrating fibroblasts are marked with green dots in FIG. 6A (AD) and FIG. 6B (AC) 48 hours after plating in Matrigel. FIG. 6C shows migration rate versus number of migrating cells, wherein green squares represent AD (n=10), blue triangles represent non-ADD (n=7), and red circles represent AC (n=9). Blue lines are separating thresholds. FIG. 6D plots the number of migrating cells as a function of disease duration in years.

FIG. 7A shows a control cell line at 2.5 hours after plating on Matrigel. FIG. 7B shows the same control cell line treated overnight with 1 µM oligomerized Aβ at 2.5 hours after plating on Matrigel, indicating impairment in network formation. FIG. 7C shows fractal dimension for the Aβ treated control cell line (green), having an AD-like phenotype. FIG. 7D shows higher lacunarity for the Aβ treated control cell line (green), indicative of AD phenotype. FIG. 7E shows an example of increasing the area per number of aggregates at 48 hours after plating due to treating with 1 µM Aβ.

FIGS. 8A and 8B show examples of AD and AC networks, respectively, comprising nodes (green arrows) and edges (blue arrows) connecting the nodes (scalebar 100 µm) 1 hour after plating on the Matrigel. FIGS. 8C and 8D show nodes with 3 or more edges and 5 edges, respectively, in an AC cell sample at increased magnification. AD cells exhibited fewer edges per node (FIG. 8E) and fewer nodes per cluster (FIG. 8F). Measurements were performed 1 hour after plating (n=10, p<0.03 two tail t-test for two samples with unequal variance).

DESCRIPTION

Particular aspects of the disclosure are described in greater detail below. The terms and definitions as used in the present application and as clarified herein are intended to represent the meaning within the present disclosure. The patent and scientific literature referred to herein is hereby incorporated by reference. The terms and definitions provided herein control, if in conflict with terms and/or definitions incorporated by reference.

The singular forms "a," "an," and "the" include plural reference unless the context dictates otherwise.

The terms "approximately" and "about" mean to be nearly the same as a referenced number or value. As used herein, the terms "approximately" and "about" should be generally understood to encompass one standard deviation from the mean of a specified amount, frequency, or value.

The present disclosure relates to peripheral diagnostic methods for screening Alzheimer's disease in patients, as well as methods of screening potential therapeutic drugs for AD, based on quantitatively measured complexity of skin-sampled fibroblast networks. Measures of the dynamics of fibroblast network complexity as disclosed herein can offer a new opportunity to diagnose AD in a patient with a minimally invasive procedure. The methods disclosed herein may provide a more accurate, simpler, and/or less costly means for screening for AD than those currently known in the art.

Skin fibroblast cells are useful in identifying characteristics of Alzheimer's disease (AD). Increasing evidence supports the so-called brain-skin axis. Mouse and human fibroblasts, for example, can be reprogrammed to become functional neurons with a combination of four transcription factors that mediate a pluripotent state. The interaction between the cutaneous nervous system and skin cells participates in skin inflammation and wound healing. Circadian clocks in peripheral skin fibroblasts are synchronized with the circadian pacemaker in the suprachiasmatic nucleus of the hypothalamus. Furthermore, there is evidence supporting a link between cutaneous (i.e. systemic) manifestations of abnormalities in amyloid metabolism and amyloid deposits in the brains of AD patients. For example, presenilin-1 is one of the major components of the γ-secretase complex. Mutation of presenilin-1 increases the activity of γ-secretase complex on the amyloid precursor protein (APP) and increases toxic amyloid beta production, which has been considered to be one of the major cause of AD. Presenilin-1 is also involved in epidermal growth factor receptor turnover. Partial loss of presenilin-1 expression may lead to seborrhoic keratoses and inflammatory skin diseases.

A variety of molecular measures in skin fibroblasts indicate AD specific deficits of protein kinase C (PKC), and extracellular regulated kinase ½ (ERK ½) signaling. This signaling has also been implicated in AD-specific deregulation of potassium channels and electrical connections in fibroblasts grown in culture. The extracellular matrix, a complex network composed of an array of macromolecules important for regulation of cell functions and tissue architecture, is deregulated in AD skin fibroblasts. Furthermore, gene expression studies using familial AD skin fibroblasts showed that the disease process may even start before the onset of cognitive decline. Familial AD fibroblasts were also found to produce excess amyloid beta in cultured fibroblasts.

Human skin fibroblast networks, like the neural networks in the AD brain, show a reduction in complexity compared to age-matched control (AC) and non-Alzheimer's disease dementia (non-ADD) cells. Measures of intercellular communication in fibroblast networks and the effect of amyloid beta on their spatiotemporal complexity can be used to screen for AD. Human skin fibroblast networks therefore provide a model of brain networks useful for accurate AD diagnosis and therapeutic drug screening. Skin fibroblast samples may be obtained from a subject through punch-biopsy or by using a surgical blade, for example.

Amyloid Beta

In some embodiments, amyloid beta is added to fibroblast cells to stimulate an AD-like phenotype for comparison with an AD-positive control.

The terms "amyloid beta peptide," "beta amyloid protein," "beta amyloid peptide," "beta amyloid," "A. beta," and "A. beta peptide" are used interchangeably herein. In some forms, an amyloid beta peptide (e.g., A. beta 39, A. beta 40, A. beta 41, A. beta 42 and A. beta 43) is an about 4-kDa internal fragment of 39-43 amino acids of the larger transmembrane glycoprotein termed amyloid precursor protein (APP). Multiple isoforms of APP exist, for example $APP^{695}$, $APP^{751}$, and $APP^{770}$. Examples of specific isotypes of APP currently known to exist in humans are the 695 amino acid polypeptide described by Kang et. al. (*Nature*, 325:733-736, 1987), designated the "normal" APP; the 751 amino acid polypeptide described by Ponte et al. (*Nature*, 331:525-527, 1988) and Tanzi et al. (*Nature*, 331:528-530, 1988); and the 770-amino acid polypeptide described by Kitaguchi et. al. (*Nature*, 331:530-532, 1988). As a result of proteolytic processing of APP by different secretase enzymes in vivo or in situ, A. beta is found in both a "short form," 40 amino acids in length, and a "long form," ranging from 42-43 amino acids in length. Part of the hydrophobic domain of APP is found at the carboxy end of A. beta, and may account for the ability of A. beta to aggregate, particularly in the case of the long form. A. beta. peptide can be found in, or purified from, the body fluids of humans and other mammals, e.g. cerebrospinal fluid, including both normal individuals and individuals suffering from amyloidogenic disorders.

The terms "amyloid beta peptide," "beta amyloid protein," "beta amyloid peptide," "beta amyloid," "A. beta," and "A. beta peptide" include peptides resulting from secretase cleavage of APP and synthetic peptides having the same or essentially the same sequence as the cleavage products. A. beta. peptides suitable for the present disclosure may be derived from a variety of sources including, but not limited to, tissues, cell lines and body fluids (e.g. sera and cerebrospinal fluid). For example, A. beta can be derived from APP-expressing cells such as Chinese hamster ovary (CHO) cells as described, for example, in Walsh et al. (*Nature*, 416:535-539, 2002). An A. beta. preparation can, for example, be derived from tissue sources (see, e.g., Johnson-Wood et al., *Proc. Natl. Acad. Sci. USA*, 94:1550, 1997) or synthesized by methods known in the art (see, e.g., Fields et al., *Synthetic Peptides: A User's Guide*, ed. Grant, W.H. Freeman & Co., New York, 1992, P77). Hence, peptides can be synthesized using the automated Merrifield techniques of solid phase synthesis with the a-amino group protected by either t-Boc or F-moc chemistry using side chain protected amino acids on, for example, an Applied Biosystems Peptide Synthesizer Model 430A or 431. Longer peptide antigens can be synthesized by known recombinant DNA techniques. For example, a polynucleotide encoding the peptide or fusion peptide can be synthesized or molecularly cloned and inserted in a suitable expression vector for the transfection and heterologous expression by a suitable host cell. A. beta peptide also refers to related A. beta sequences that result from mutations in the A. beta. region of the normal gene.

An amyloid beta-induced abnormality in cell morphology may be used as a confirmatory test for either the presence or absence of Alzheimer's Disease. For example, a negative amyloid beta-index response can indicate the presence of disease, while a positive response can indicate the absence of disease. That is, if an AD morphology phenotype is induced in cells upon incubation or contact with an amyloid beta peptide, this is indicative of the absence of AD in the test cells or subject being tested. In contrast, if little or no change in phenotype is induced in cells upon incubation or contact with an amyloid beta peptide (i.e., no statistically significant change in the measurement of network complexity), this is indicative of the presence of AD in the test cells or subject being tested.

Amyloid beta (1-42) (i.e., Aβ (1-42)) and/or any other amyloid beta fragments may be used herein, including, but not limited to, (1-39), (1-40), (1-41), (1-43), (25-35), (16-22), (16-35), (10-35), (8-25), (28-38), (15-39), (15-40), (15-41), (15-42), and (15-43).

Cell Culture

The AD, AC, and non-ADD cell(s) or cell sample(s) may be cultured or incubated in a medium comprising a protein mixture, such as a gelatinous protein mixture. In at least some embodiments, the cells are cultured after adding amyloid beta.

In some embodiments, the culture medium comprises a preparation. In some embodiments, the preparation is solubilized. In at least one embodiment, the preparation is extracted from a tumor, such as the Engelbreth-Holm-Swarm (EHS) mouse sarcoma, and is rich in extracellular matrix (ECM) proteins. Such preparations may, for example, comprise at least one of laminin, collagen IV, heparan sulfate proteoglycans, and entactin/nidogen. A non-limiting example suitable for the present disclosure is Matrigel™, which is the trade name (BD Biosciences) for a gelatinous protein mixture secreted by EHS mouse sarcoma cells. This mixture resembles the complex extracellular environment found in many tissues, and may be used as a substrate for cell culture. Matrigel comprises laminin, collagen IV, heparan sulfate proteoglycans, and entactin 1. At 37° C., Matrigel polymerizes to produce biologically active matrix material resembling the mammalian cellular basement membrane.

In some embodiments of the present disclosure, the preparation further comprises TGF-beta, epidermal growth factor, insulin-like growth factor, fibroblast growth factor, tissue plasminogen activator, and/or other growth factors that may or may not occur naturally in a tumor. In some embodiments, TGF-beta, epidermal growth factor, insulin-like growth factor, fibroblast growth factor, tissue plasminogen activator, and/or other growth factors occur naturally in a tumor, such as the EHS mouse sarcoma tumor. BD Matrigel™ Matrix Growth Factor Reduced (GFR), for example, may be suitable for applications requiring a more highly defined basement membrane preparation of the gel substrate.

The preparation may comprise an ECM protein preparation effective for the attachment and differentiation of both normal and transformed anchorage dependent epithelioid and other cell types. Examplary cell types include, but are not limited to, neurons, hepatocytes, Sertoli cells, chick lens, and vascular endothelial cells. The ECM protein preparation may influence gene expression in adult rat hepatocytes as well as three dimensional culture in mouse and human mammary epithelial cells. The preparation may, for example, serve as the basis for tumor cell invasion assays, support in vivo peripheral nerve regeneration, and/or provide a substrate for the study of angiogenesis both in vitro and in vivo. The ECM protein may also support in vivo propagation of human tumors in immunosupressed mice.

In some embodiments of the present disclosure, a volume of chilled ECM protein is dispensed onto tissue culture labware. As used herein, the term "chilled" refers to a temperature less than room temperature, for example, less than about 15° C., less than about 10° C., less than about 5° C., e.g., a temperature of about 4° C. When incubated at an elevated temperature, the ECM proteins may self-assemble to produce a thin film that covers the surface of the labware. As used herein, the term "elevated" refers to a temperature above room temperature, such as above about 20° C., above about 25° C., above about 30° C., above about 35° C., e.g., a temperature of about 37° C., which is approximately the average temperature of the human body.

Cells cultured on ECM protein may demonstrate complex cellular behavior otherwise difficult to observe under laboratory conditions. For example, endothelial cells can create intricate spiderweb-like networks on ECM protein coated surfaces but not on plastic surfaces. Such networks are suggestive of the microvascular capillary systems that suffuse living tissues with blood, such that ECM proteins assist in the observation of that process.

In some embodiments, greater volumes of ECM proteins are used to produce thick three-dimensional gels for culturing cells. For example, thick gels may be useful in inducing cells to migrate from the surface to the interior of the gel. In some embodiments, this migratory behavior can serve as a model for tumor cell metastasis. In some embodiments, the culture medium comprises a layer with a thickness between about 1.0 mm and about 2.0 mm, such as about 1.5 mm or about 1.8 mm. The amount of culture medium may also be expressed as the volume (V) in a well plate according to the relationship $V=(\pi r^2)h$, wherein h is the thickness of the layer and r is the radius. In some embodiments, for example, the volume of culture medium may range from about 400 μl to about 800 μl, such as about 700 μl, with r=11.05 mm.

Without being bound by theory, it is believed that the ability of ECM proteins to stimulate complex cell behavior may result from a heterogeneous composition. In some embodiments, the chief components of ECM proteins are structural proteins, such as laminin and collagen, which present cultured cells with the adhesive peptide sequences they would encounter in their natural environment. Some embodiments of the present disclosure employ growth factors that can promote differentiation and proliferation of many cell types. ECM proteins may also contain numerous other proteins in small amounts.

Figure 1:
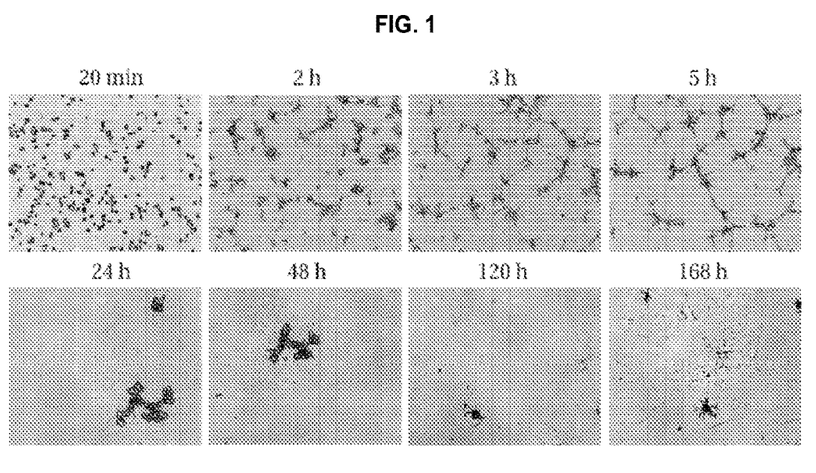
FIG. 1 shows AD fibroblast dynamics on a thick layer of Matrigel, illustrating fast (top row) and slow (bottom row) dynamics. Note that aggregates appear 24 hours and 48 hours after plating.

Within 1 to 2 hours in culture, skin fibroblast cells may connect to form measurable networks. This condition provides a physiologically relevant environment for studying cell morphology, cellular biochemical functions, cell motility or invasions, and/or gene expression. These networks degenerate over time (e.g., from about 5 hours up to about 48 hours) wherein the edges (connections) between nodes retract to leave behind measurable aggregates. As the cell(s) and/or cell fibroblast network changes, images may be taken to gather quantitative, qualitative, and semi-quantitative information. In some embodiments of the present disclosure, images are taken at about 20 minutes, about 30 minutes, about 45 minutes, about 1 hour, about 1.5 hours, about 2 hours, about 2.5 hours, about 3 hours, about 5 hours, about 8 hours, about 10 hours, about 12 hours, about 24 hours, about 36 hours, about 48 hours, about 60 hours, or even about 72 hours or more after culturing. FIG. 1 shows an example of fibroblast cell dynamics for AD cells plated on a thick layer of Matrigel (1.8 mm). AC cell lines exhibit similar dynamics, but AC cell lines tend to show a greater number of aggregates that are smaller (see, e.g., Example 1 and FIGS. 2D, 3B, 5B, and 6B).

In some embodiments, certain characteristics of the image(s) may be assigned values according to one or more of the following methods to quantitatively assess patterns in fibroblast network dynamics.

1. Integrated Score

Eight parameters are used to separate AD cells from AC, non-ADD cells after culturing (e.g., 48 hours after plating on Matrigel), listed in Table 1.

TABLE 1

Parameters for integrated score

| | Parameter | Value |
|---|---|---|
| 1. | Existence of large aggregates | −1 or 0 |
| 2. | Attachment of cells to the aggregates | −1 or 0 |
| 3. | Evidence of aggregates growing | −1 or 0 |
| 4. | Small number of aggregates (<10 on a 10x image) | −1 or 0 |
| 5. | Large number of aggregates (>10 on a 10x image) | +1 or 0 |
| 6. | Measurable edges within networks. | +1 or 0 |
| 7. | Evidence of cell migrations | +1 or 0 |
| 8. | Closeness to percolation limit (cells form continuous streams) | +1 or 0 |

From these eight parameters, a semi-quantitative score ("integrated score") is calculated as follows. The first four parameters (1-4) are specific to Alzheimer's disease with a score of "−1" for each if present and "0" if absent. The last four parameters (5-8) are specific to non-ADD and AC with a score of "+1" if present and "0" if absent. The integrated score is calculated as the sum of all eight values. If the integrated score is positive or zero, the cells are AC or non-ADD. If the integrated score is negative, the cells are AD. In some embodiments, the method can be fully automated using known image processing techniques.

In some embodiments of the present disclosure, the integrated score is used to separate AD fibroblasts from age matched controls (AC) and/or non-Alzheimer's dementia (non-ADD). In some embodiments, the integrated score is calculated for cell images taken 48 hours after culturing (e.g., plating on Matrigel).

In some embodiments of the present disclosure, a positive diagnosis for AD is made if the integrated score for Aβ-treated test cells is less than the integrated score for non-treated test cells. In some embodiments, a positive diagnosis for AD is made if the difference in integrated score between Aβ-treated test cells and AD control cells is not statistically significant, i.e., more than one standard deviation.

2. Area Per Number of Aggregates

Parameters 4 and 5 used for the integrated score may also be expressed as aggregate area per number of aggregates (<Area>/number of aggregates) to provide a more quantitative measure of morphology. AD cells tend to form larger, isolated aggregates, whereas normal controls and non-ADD fibroblasts tend to form numerous smaller aggregates. Thus, the <Area>/number of aggregates value is generally considerably higher for AD cells than for AC and/or non-ADD cells.

The <Area>/number of aggregates may be calculated from the average aggregate area $<A>_i$ and number of aggregates $N_i$ determined from each image by averaging the ratio $<A>_i/N_i$. See, e.g., Example 1.3 and FIG. 3C. This can be done by any suitable method, such as fitting an ellipse across the aggregate. The aggregates can then be counted on the images. Counting and/or area calculation may be done manually, or may also be automated, for example, by image processing techniques.

In some embodiments of the present disclosure, a positive diagnosis for AD is made if the <Area>/number of aggregates for Aβ-treated test cells is greater than the <Area>/number of aggregates for non-treated test cells. In some embodiments, a positive diagnosis for AD is made if the difference in <Area>/number of aggregates between Aβ-treated test cells and AD control cells is not statistically significant.

3. Fractal Dimension

Complexity of human skin fibroblast networks can be quantified by computing their fractal dimensions. Fractal analysis utilizes the complexity of the networks as means for distinguishing AD, AC, and non-ADD cells. Fibroblast cells obtained from patients suffering from AD have a statistically significant lower fractal dimension than AC cells when grown in tissue culture. The complexity of the networks measured by fractal dimension is also markedly different for fibroblasts taken from AD as compared to AC and non-ADD fibroblasts. Thus, a reduced complexity of human skin fibroblast networks AD cases provides distinctions from AC and non-ADD cases.

After network degeneration (e.g., about 48 hours), cells migrate and reach confluence within a few days. This recovery is captured by a linear increase in fractal dimension. Recovery as measured by the slope and intercept of the fractal curves therefore shows quantifiable differences between AD, non-ADD, and AC cells.

Fractal dimension can be generalized to $N(s)=(1/s)^D$, wherein D is the dimension and can be an integer or non-integer. Taking logarithms of both sides gives $\log(N(s))=D \log(1/s)$, such that the fractal dimension can be determined by plotting $\log(N(s))$ against $\log(1/s)$. If the slope is a non-integer, the dimension is a fractional (fractal) dimension.

The fractal dimension may be calculated using a standard box counting procedure after raw images (e.g., digital images) are filtered through an edge detection procedure that uses, for example, the difference of two Gaussians. Edge detection is a term used in the field of image processing, particularly in the areas of feature detection and feature extraction, to refer to algorithms which aim at identifying points in a digital image at which, for example, the image brightness changes sharply or has other discontinuities.

It can be shown that under rather general assumptions for an image formation model, discontinuities in image brightness are likely to correspond to one or more of discontinuities in depth, discontinuities in surface orientation, changes in material properties and variations in scene illumination.

Applying an edge detector to an image may lead to a set of connected curves that indicate the boundaries of objects, the boundaries of surface markings as well curves that correspond to discontinuities in surface orientation. Thus, applying an edge detector to an image may significantly reduce the amount of data to be processed, and may therefore filter out information that may be regarded as less relevant while preserving the important structural properties of an image. If the edge detection step is successful, the subsequent task of interpreting the information content in the original image may therefore be substantially simplified.

Methods for edge detection can generally be grouped into two categories: search-based and zero-crossing based. The search-based methods detect edges by first computing a measure of edge strength, usually a first-order derivative expression such as the gradient magnitude, and then searching for local directional maxima of the gradient magnitude using a computed estimate of the local orientation of the edge, usually the gradient direction. The zero-crossing based methods search for zero crossings in a second-order derivative expression computed from the image in order to find edges, usually the zero-crossings of the Laplacian or the zero crossings of a nonlinear differential expression. As a pre-processing step to edge detection, a smoothing stage, for example Gaussian smoothing, may be applied. In other embodiments noise filtering algorithms may be employed.

The edge detection methods that have been published mainly differ in the types of smoothing filters that are applied and the way the measures of edge strength are computed. As many edge detection methods rely on the computation of image gradients, they also differ in the types of filters used for computing gradient estimates in the x- and y-directions.

In one embodiment of the present disclosure, the fractal dimension is determined using a box counting procedure wherein the image is covered with boxes, for example, by a computer. The goal is to determine how the number of boxes needed to cover the image changes with the size of the boxes. If the object is 1-dimensional, such as a line, the relationship is $N(s)=(1/s)^1$ as described above, and so on for higher dimensions. In some embodiments, the box counting procedure is implemented on a computer using digital images of cell samples.

In some embodiments of the present disclosure, a positive diagnosis for AD is made if the fractal dimension for $A\delta$-treated test cells is less than the fractal dimension for non-treated test cells. In some embodiments, a positive diagnosis for AD is made if the difference in fractal dimension between $A\delta$-treated test cells and AD control cells is not statistically significant.

4. Lacunarity

As used herein, "lacunarity" refers to a measure of how a fractal fills space. It is used to further classify fractals and textures which, while they may share the same fractal dimension, appear very visually different. Dense fractals have a low lacunarity. As the coarseness of the fractal increases, so does the lacunarity; intuitively from lacuna meaning "gap" (more gaps=higher lacunarity). Lacunarity is typically represented by L:

$$L(r) = \frac{\sum_{m=1}^{r2} m^2 P(m,r) - \left(\sum_{m=1}^{r2} m P(m,r)\right)^2}{\left(\sum_{m=1}^{r2} m P(m,r)\right)^2}$$

Lacunarity is a complementary measure for complexity discrimination that quantifies the gaps in cellular networks. AD cell lines show an increased average lacunarity when compared with cell lines from AC and non-ADD individuals.

The lacunarity analysis method presently disclosed quantifies gaps of the fibroblast patterns as a complementary measure of complexity used as a second level of discrimination. The average lacunarity is higher for AD fibroblasts in comparison to AC and non-ADD fibroblasts. Typically the lacunarity increases and peaks when the network degeneration is maximized, i.e., only isolated aggregates are visible. Lacunarity drops as network regeneration starts.

In some embodiments of the present disclosure, a positive diagnosis for AD is made if the lacunarity for $A\beta$-treated test cells is greater than the lacunarity for non-treated test cells. In some embodiments, a positive diagnosis for AD is made if the difference in lacunarity between $A\beta$-treated test cells and AD control cells is not statistically significant.

5. Cell Migration

Cell migration allows for distinguishing between AD, AC, and non-ADD cells. A freely migrating cell is defined as a cell that is not attached to aggregates. Freely migrating cells may be counted at different times during culturing. For example, for times $N_1$ and $N_2$, the migration rate is calculated as $R=(N_2-N_1)/\Delta T$, where $\Delta T$ is the time interval between cell migration counts. For example, in some embodiments, the number of freely migrating cells may be counted about 24 hours after plating, such as about 36 hours, about 48 hours, about 50 hours, about 52 hours, about 55 hours, about 57 hours, or about 60 hours after plating. In at least one embodiment, the migration rate is counted for times $N_1=48$ hours after plating and $N_2=55$ hours after plating. In some embodiments, the initial cell density is controlled. In at least one embodiment, the initial cell density is controlled to about 50 cells/mm³.

In some embodiments of the present disclosure, a positive diagnosis for AD is made if the number of migrating cells for $A\beta$-treated test cells is less than the number of migrating cells for non-treated test cells. In some embodiments, a positive diagnosis for AD is made if the difference in number of migrating cells between $A\beta$-treated test cells and AD control cells is less than one standard deviation from the mean. In at least one embodiment, a migration rate lower than about 0.3 $hr^{-1}$ is indicative of AD.

The five analysis methods described above (i.e., integrated score, area per number of aggregates, fractal dimension, lacunarity, and cell migration) may be used alone or in combination. In some embodiments, for example, the integrated score and area per number of aggregates are calculated. In another embodiment, for example, a combination of fractal analysis, lacunarity analysis, and cell migration analysis is used. In another embodiment, the integrated score and average aggregate area per number of aggregates are calculated in addition to applying fractal analysis, lacunarity analysis, and/or cell migration analysis. In some embodiments, the methods disclosed herein screen not only AD cells from AC cells, but also screen AC cells from non-ADD cells such as Huntington's disease (HD) and/or Parkinson's disease (PD).

In some embodiments, a positive diagnosis for AD is made when two or more of the analysis methods independently give a positive diagnosis for AD. In other embodiments, a positive diagnosis for AD is made when all analysis methods (e.g., two different techniques, three different techniques, four different techniques, or five different techniques) independently give a positive diagnosis for AD.

In some embodiments of the present disclosure, false positives and/or false negatives may be avoided and/or minimized by setting a diagnosis threshold at a certain multiple of population standard deviation(s) for any of the above mentioned variables.

Morphological Analysis as a Measure of Intercellular Communication

Analysis of the complexity of fibroblast networks provides information regarding intercellular communication. Networks are ubiquitous in nature and offer a framework for understanding connectivity arising from interactions such as those between computers on the Internet, neurons in an organism, elements in a power grid, and among people. In AD, neuronal networks are progressively disrupted due to synaptic loss. Human skin fibroblast networks, like neural networks in AD brains, are also disrupted and may be characterized by quantitative, physical measurements such as the number of edges per node or the number of nodes per cluster. A node is a connection point (e.g., redistribution point or communication endpoint), and an edge is a connection between two nodes. A cluster or sub-network is a group of nodes continuously connected with one other.

The number of edges per node in cultured cell samples may be counted as a measure of intercellular communication. In some embodiments, the number of edges per node of cultured cells is counted at a pre-determined time period, such as a time ranging from about 1 hour to 5 hours after plating. In at least one embodiment, the number of edges per node is counted about 1 hour after plating.

While the methods herein describe fibroblast cells, morphological analysis of other cells such as blood cells or neural cells is also contemplated.

The following examples are intended to illustrate the present disclosure without, however, being limiting in nature. It is understood that the skilled artisan will envision additional embodiments consistent with the disclosure provided herein.

EXAMPLES

Example 1. Comparison of AD, AC, and Non-ADD Cells 1.1: Cell Preparation and Imaging Experiments were carried out using 33 human skin fibroblasts from the Coriell Institute for Medical Research (Camden, N.J.) (Tables 2 and 3).

TABLE 2

Human skin fibroblast cells analyzed (AC = age-matched controls; AD = Alzheimer's disease; HD = Huntington's disease; PD = Parkinson's disease).

| Diagnostic criteria | Rule AD IN AD patients | Rule AD OUT Non-ADD | Non-Demented Controls | Total |
|---|---|---|---|---|
| Autopsy confirmed | 7 | 1 PD | — | |
| Genetic & Family History | 3 | 7 HD + 1 PD | — | |
| Clinical diagnosis ONLY | 3 | — | — | |
| Total | 13 | 9 | 11 AC | 33 |
| Well characterized | 10 | 9 | 11 | 30 |

TABLE 3

Human skin fibroblast cells analyzed.

| AC (n = 11) | AD (n = 13)[3] | Non-ADD (n = 9)[5] |
|---|---|---|
| AG12438 | AG05770[1] | GM02173[5] |
| AG12927 | AG08245[1] | GM00305[5] |
| AG07714 | AG06263[3] | GM05030[5] |
| AG04146 | AG08170[2] | GM05031[5] |
| AG04461 | AG06840[2] | GM06274[5] |
| AG11734 | AG04159[2] | GM02165[5] |
| AG05840 | AG06844[1] | GM02167[5] |
| AG07123 | AG06869[1] | ND27760[5] |
| AG09977 | AG07374[3] | AG08395[4] |
| AG12998 | AG08527[1] | |
| AG11358 | AG10788[1] | |
| | AG11368[1] | |
| | AG05810[3] | |

[1]Autopsy confirmed
[2]Genetic & family history
[3]Clinical diagnostic ONLY
[4]Autopsy confirmed
[5]Genetic & family history Cells were plated on a thick layer (~1.8 mm) of Matrigel on 12 well plates. The cell lines analyzed (30/33) were mostly well characterized based on either autopsy or genetic family history (Table 2). Similar results were obtained with fibroblasts freshly taken from the clinic.

The initial cell density was controlled to be 50 cells/mm³, and homogenized with 1.5 ml Dulbecco's Modified Eagle Medium with 10% fetal bovine serum and 1% penicillin/streptomycin (PS) for each well. Cells were kept in a $CO_2$ water-jacket incubator (Forma Scientific) up to 7 days after plating.

Images of the cellular networks were captured with an inverted microscope controlled by a computer using a 10× objective. See FIG. 1. Five images were taken per well, typically with three wells per cell line. Images were acquired every hour on the first day, every other hour on the second day, and three times a day for the remaining three days. The images were processed with ImageJ, a freely available software from NIH (http://rsbweb.nih.gov/ij/). Fractal and lacunarity analyses were done with the FrcLac_2.5 plugin. Custom scripts were written for automatic image analyses. The aggregates were manually fitted with ellipses using Micron 2.0 software and their area and number recorded. The automatic script developed for ImageJ agrees well with manual ellipse fitting; these two approaches were within one standard deviation of each other.

1.2: Integrated Score

Figure 2:
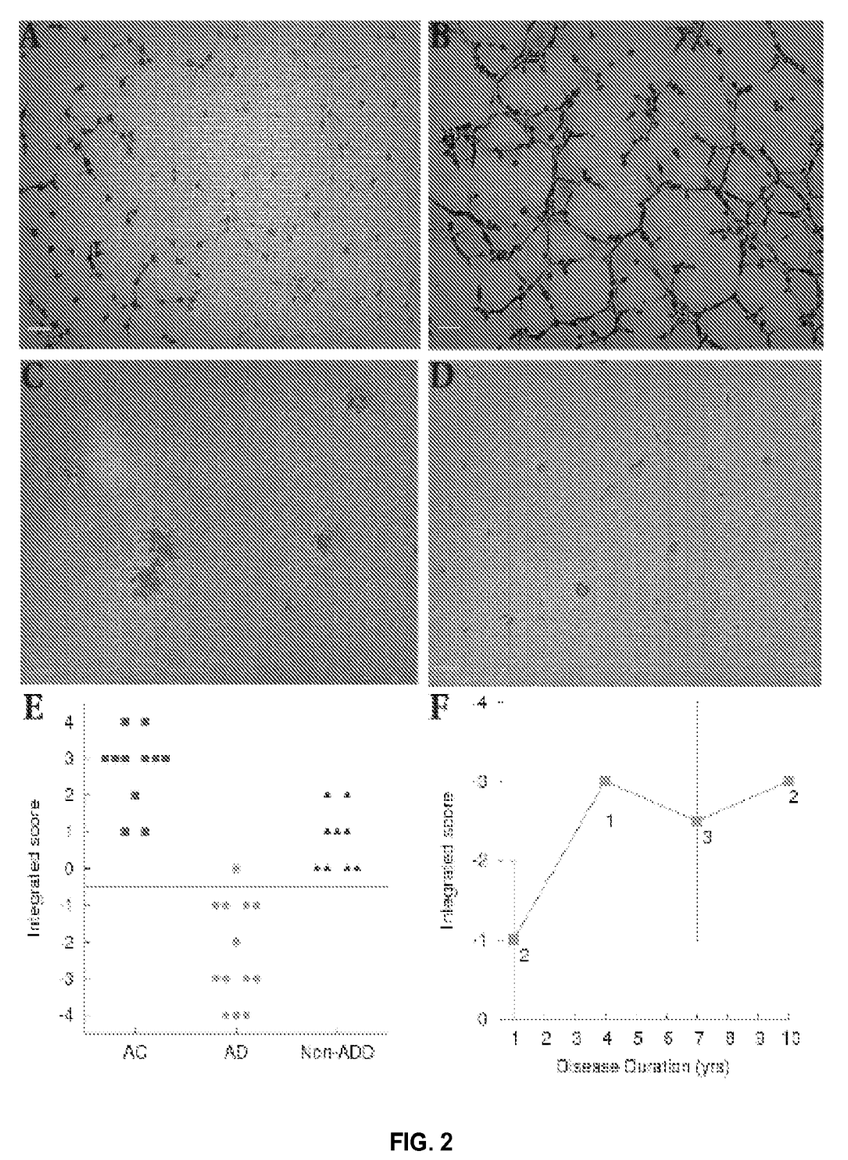
FIG. 2 shows images of cultured human skin fibroblast AD and AC cells, and integrated score values for AC, AD, and non-ADD cells. AD cells after plating in Matrigel are shown in FIG. 2A (1 hour) and FIG. 2C (48 hours); AC cells after plating are shown in FIG. 2B (1 hour) and FIG. 2D (48 hours); scalebar=100 µm.

Images showing typical skin fibroblast cell network formation and degeneration of two cell lines prepared as described in Example 1.1 are shown in FIGS. 2A-2D. AD cell lines (FIG. 2A) were slower in forming networks when compared with age-matched controls (FIG. 2B). The edges of these networks started to degenerate approximately 5 hours after plating when they became progressively thinner until they eventually disappeared. As a result of edge retraction, only the nodes of the network remained as cellular aggregates. Aggregates were visible as soon as 24 hours after plating. FIGS. 2C and 2D show images taken at 48 hours for the AD and AC cells, respectively.

Eight parameters were used to distinguish AD, AC, and non-ADD fibroblasts 48 hours after plating on Matrigel by calculating the integrated score (the sum of all eight values). A positive integrated score or score of zero indicates that the cells are AC or non-ADD; a negative intregrated score indicates that the cells are from patients with AD.

The population data for the integrated scores of skin cell fibroblasts at 48 hours after plating shows good separation between AD, AC, and non-ADD cells (FIG. 2E). The integrated score appears to correlate with the duration of Alzheimer's disease, becoming more negative as the disease duration increases (FIG. 2F).

1.3: Average Area Per Number of Aggregates

Diagnostic accuracy increased when two of the eight parameters from the integrated score were expressed in a measure of the average aggregate area per number of aggregates (<Area>/number of aggregates). To calculate this value, an average aggregate area $<A>_i$ and a number of aggregates $N_i$ were first calculated for each image. The ratio $<A>_i/N_i$ was then evaluated. Five images per well were typically used, and an average area per number for each well determined according to $$\sum_{i=1}^{5} \frac{\langle A \rangle_i}{N_i}.$$

Figure 3:
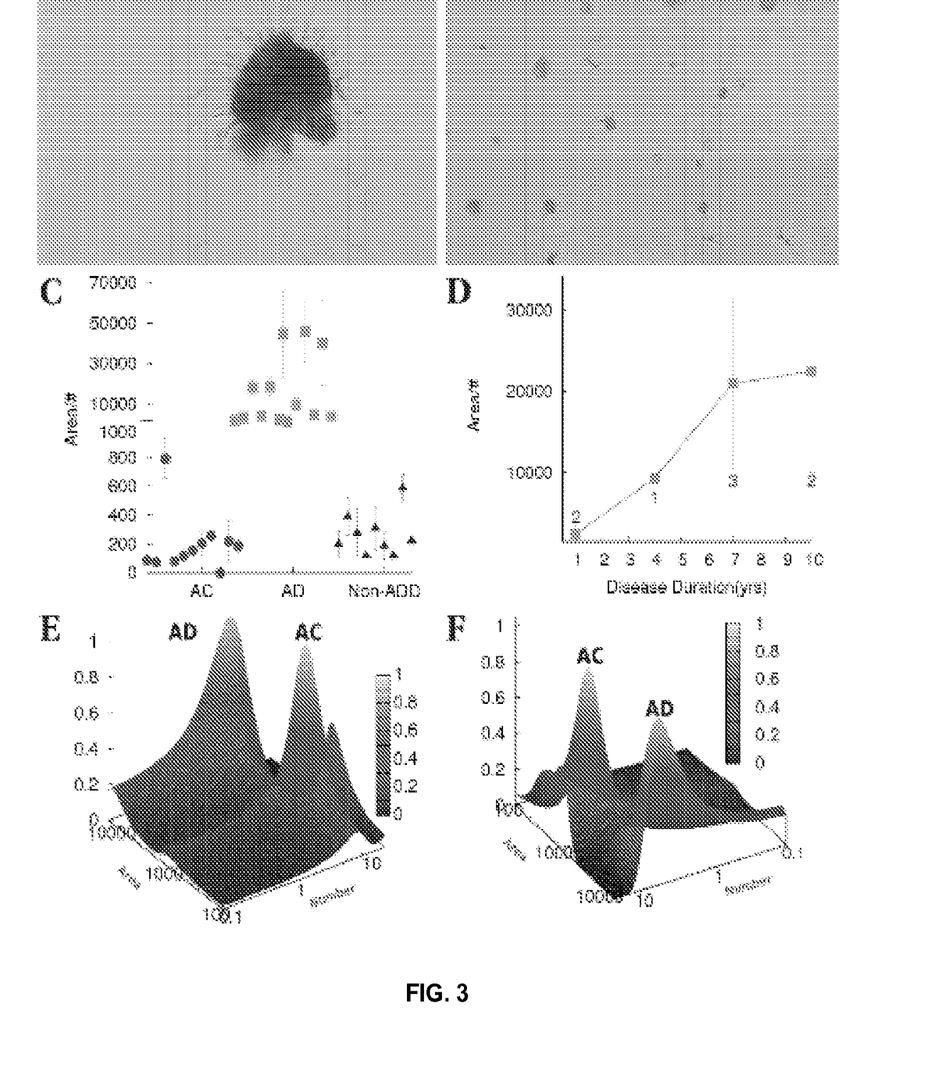
FIG. 3 illustrates aggregate area per number of aggregate (Area/#) analysis for AD, AC, and non-ADD cells.

The three wells were averaged according to $$\sum_{w=1}^{3}\left(\sum_{i=1}^{5}\frac{\langle A\rangle_i}{N_i}\right)_w,$$

which is the number shown for each cell line in FIG. 3C. This measure was considerably higher for AD than for AC and non-ADD (diagnostic accuracy 96%, N=33 ($n_{AD}$=13, $n_{AC}$=11, and $n_{non-ADD}$=9) p<0.000001 for AD vs AC, and p<0.00001 for AD vs Non-ADD).

Figure 5:
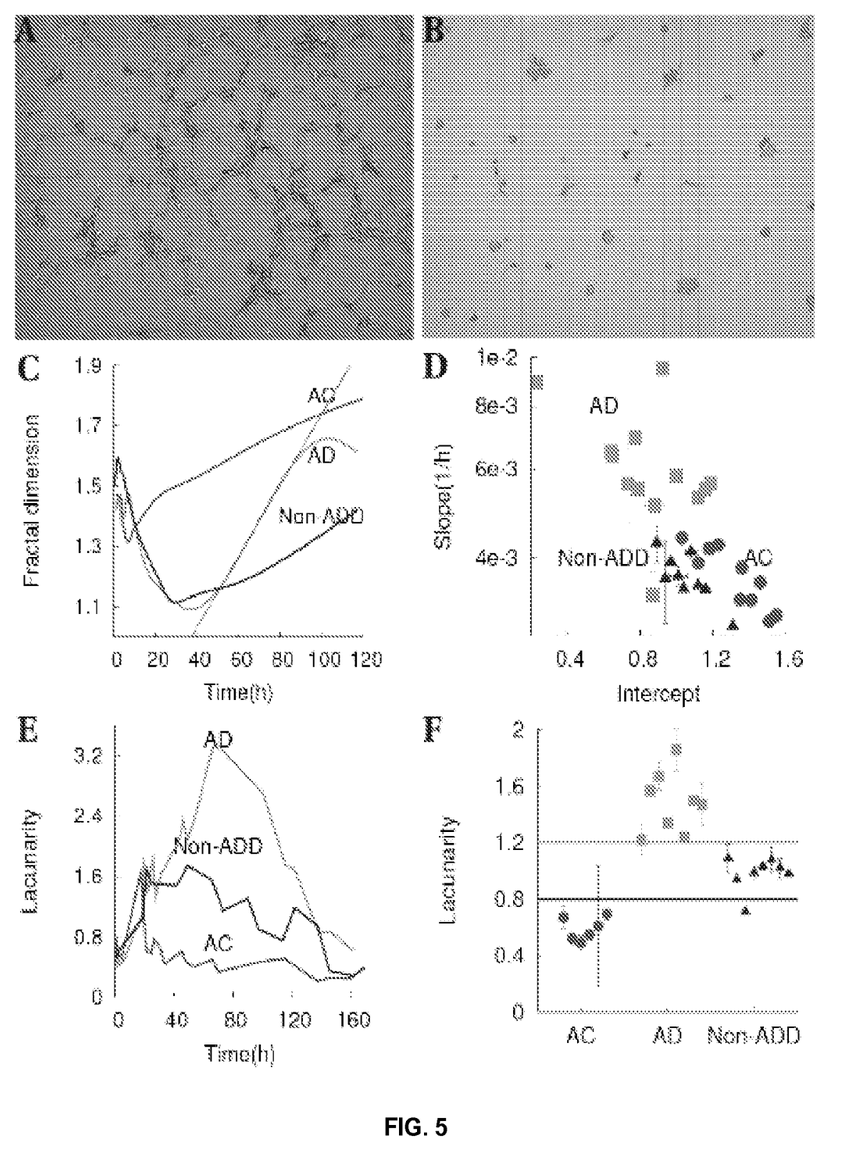
FIG. 5 illustrates fractal and lacunarity analysis.

The AD cells show large isolated aggregates (FIGS. 3A and 5A), whereas the normal controls (AC) and non-ADD fibroblasts show numerous smaller aggregates (FIGS. 3B and 5B).

Figure 4:
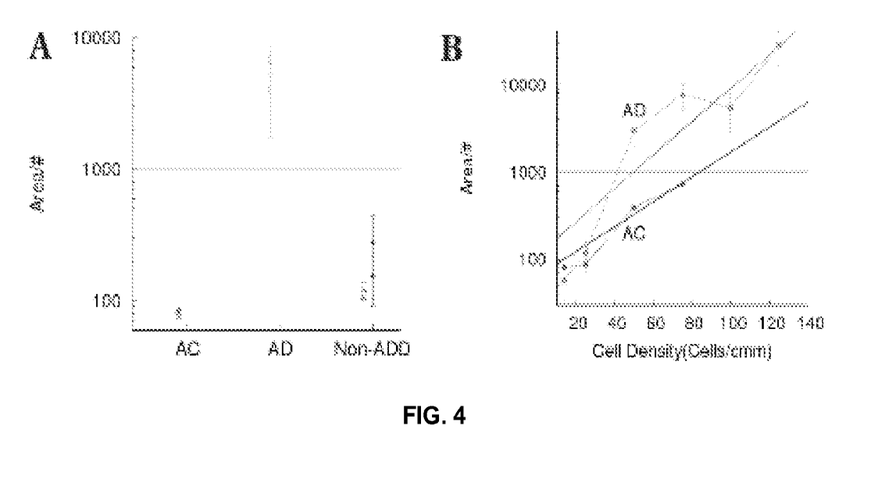
FIG. 4 shows precision in the determination of average aggregate area per number of aggregates.

The population data (FIG. 3C) show no overlap between AC, non-ADD, and AD. The <Area>/number of aggregates increased with AD disease duration (FIG. 3D). The probability distribution of the cellular aggregates as a function of area and number at 48 hours shows that the AD group (n=13) separates well from AC group (n=11). Values for area and number of aggregates were binned into intervals inversely proportional to the density of points, fit with Gaussian functions for each variable, and then integrated into normalized distributions. The peak probability value for the AD population was at N=5, Area=12370; while the AC population had a peak at N=8, Area=1004. The standard deviations for the AC population were $\sigma_N$=2.3, $\sigma_{Area}$=451 while for the AD population were $\sigma_N$=2.6, $\sigma_{Area}$=5000. These standard deviations indicate that the probability distributions for the numbers of aggregates have some overlap, while the probability distributions for the areas have no overlap at half-width. Therefore, a simple method of increasing separability between AD and AC populations was to collapse the two variables into one by dividing them as area/number. In this way the dynamic range increases from 8/5=1.6 for N, and 12370/1004=12.3 for area, to 19.7 for Area/N. Repeatability of results is shown in FIG. 4.

Similar results for <Area>/number of aggregates were obtained for 4 fresh samples from the clinic. The threshold for different cell types (e.g., AC and AD) for the fresh samples seems to be higher (Area/#~2000) when compared with Coriell samples (Area/#~1000). See FIG. 4A.

AC cells may be further distinguished from non-ADD cells by fractal analysis (Example 1.4), lacunarity analysis (Example 1.5), and cell migration analysis (Example 1.6).

1.4: Fractal Dimension Analysis

The dynamics of spatiotemporal complexity such as network formation (FIG. 5A), network degeneration (FIG. 5B) and recovery can be measured by fractal and lacunarity curves (FIGS. 5C and 5D). AD fibroblast networks measured by these physical parameters were markedly less complex when compared to AC and non-ADD networks. After network degeneration (~48 h, FIG. 5B), cells migrated and within a few days approached confluence. This recovery is captured by a linear increase in fractal dimension as shown in FIG. 5C. The slope versus the intercept of each curve that tracks fractal dimension as a function of time is markedly different in the three groups AC, AD, and non-ADD (96% accuracy, n=33 ($n_{AD}$=13, $n_{AC}$=10, $n_{non-ADD}$=9); p<0.0001 for AD vs AC, and p<0.00001 for AD vs non-ADD). The fractal analysis discriminated not only between AD and AC, non-ADD cells; but also between AC and non-ADD cells (p<0.01) (FIG. 5F).

1.5: Lacunarity Analysis

Lacunarity is a complementary measure for fractal dimension. It is used as a second level of complexity discrimination that quantifies the gaps in fibroblast patterns. The average lacunarity of the fibroblasts was higher for fibroblasts taken from AD patients when compared to AC and non-ADD fibroblasts. Typically, the lacunarity increases and peaks when the network degeneration is at a maximum, i.e., when only isolated aggregates are visible near the time point of 48 hours (FIGS. 5B and 5D). Lacunarity decreased as the cells migrated and became more confluent. The population data in FIG. 5F show that average lacunarity like fractal analysis discriminated not only between AD and AC, non-ADD cells; but also between AC and non-ADD cells (p<0.01).

1.6: Cell Migration

Figure 6:
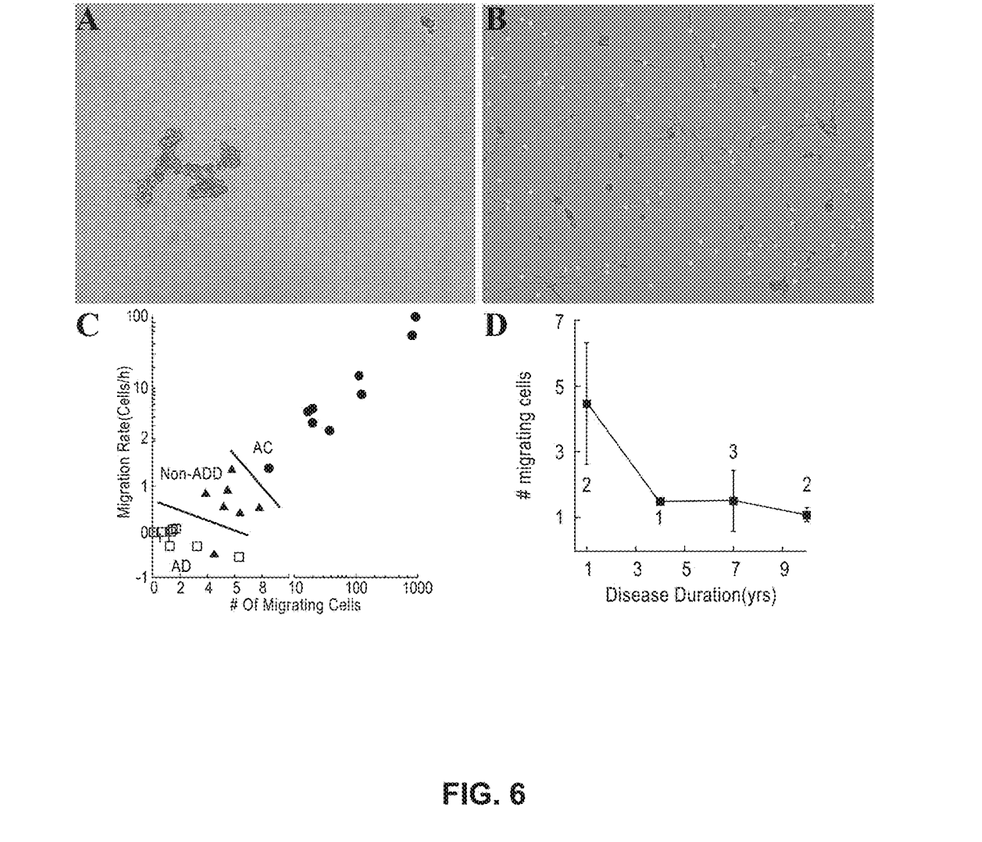

Freely migrating cells were counted at 48 hours ($N_1$) and approximately 7 hours later ($N_2$), where the migration rate was calculated as R=($N_2$−$N_1$)/ΔT with ΔT=the time interval between counts. Freely migrating cells (i.e., cells not attached to aggregates) are depicted by the green dots in FIGS. 6A (AD cells) and 6B (AC cells). The number of migrating cells was reduced in AD fibroblasts in comparison to normal controls.

The population data in FIG. 6C shows that AD fibroblasts (green) and non-ADD fibroblasts (blue) had significantly fewer migrating cells and lower rate of migration when compared with AC fibroblasts. AD fibroblasts (green) showed the smallest number of migrating cells and the lowest migration rate, whereas AD fibroblasts (red) show the highest number of migrating cells and the highest migration rate. Interestingly, non-ADD fibroblasts separated (with one exception) from AD and AC cells. The number of migrating cells also appeared to decrease with increasing duration of Alzheimer's disease as shown in FIG. 6D.

1.7: Accuracy, Specificity, and Sensitivity

The five analysis methods (Examples 1.2-1.6) resulted in an average rate of diagnostic accuracy of 96.8% (Table 4), ranging from 95% for the average lacunarity and 100% for the average area per number of aggregates. For the integrated score and fractal analysis (slope versus intercept), the rate of success was 97%, while for the cell migration the rate of success was 96%.

Sensitivity is defined as the probability that the method is positive when applied to a group of patients with the disease, Sn=TP/(TP+FN), where TP and FN are the number of true positive and false negative results, respectively. For the five methods combined, the average sensitivity was 96.8%, ranging from 92% for the integrated score and fractal analysis to 100% for the <Area>/number of aggregates, lacunarity analysis, and cell migration analysis.

TABLE 4

| Method | Accuracy (%) | Sensitivity (%) | Specificity (%) | Positive predictive value (%) | Negative predictive value (%) |
|---|---|---|---|---|---|
| Integrated score | 97 | 92 | 100 | 100 | 95 |
| Average area per number of aggregates | 100 | 100 | 100 | 100 | 100 |
| Fractal analysis | 97 | 92 | 100 | 100 | 95 |
| Lacunarity analysis | 95 | 100 | 100 | 90 | 100 |
| Cell migration analysis | 96 | 100 | 94 | 90 | 100 |

The five methods gave an average specificity of 98.8% with only one value different than 100% for cell migration which shows a specificity of 94%.

Overall, the five methods provided an average accuracy of 96.8%, an average sensitivity of 96.8%, and an average specificity of 98.8%.

Example 2: Amyloid Beta

Initial experiments suggest that some of the differences previously observed of network complexity between AD and AC fibroblasts may be due to oligomerized beta amyloid (Aβ).

Skin fibroblasts were obtained from the Coriell Institute for Medical Research (Camden, N.J.). Banked fibroblasts from Alzheimer's disease (AD) patients and age match controls (AC) were maintained and cultured in T25 culture flasks with DMEM culture medium containing 10% fetal bovine serum (FBS) and 1% penicillin/streptomycin, and placed in a 5% $CO_2$ and 37° C. incubator. All flasks were regularly examined, and after 7-10 days the cultures became confluent. The total number of cell passages was not allowed to exceed 16. Cells were trypsinized, counted (cells/$mm^3$) with a cell counting chamber (Hausser Scientific). Samples of the AC and AD cells were treated overnight with 1 μM oligomerized amyloid beta (Aβ). The treated and untreated AC and AD cells were plated in 12 well plates on a thick layer (~1.8 mm) of Matrigel. An average number of 9 counting squares was used for cell counting, with 50 cells/$mm^3$.

Five 10× images per well were used (center, up, down, left right) for quantitative image analysis. Three wells for each cell line were typically used. A cell culture microscope (Westover Digital AMID Model 2200) was used for recording the images in .png format under 10× magnification. GNU Image Manipulation (GIMP2.6) and ImageJ (1.45a) software were used for image analysis. For fractal analysis, the plug in for ImageJ, FracLac 2.5, was used with the option of standard box counting. The raw .png images were automatically despeckled 3 times, filtered, smoothed, and made binary using custom scripts for ImageJ. The binary images were saved and imported in ImageJ for fractal and lacunarity analyses with the plug-in FracLac.

Figure 7:
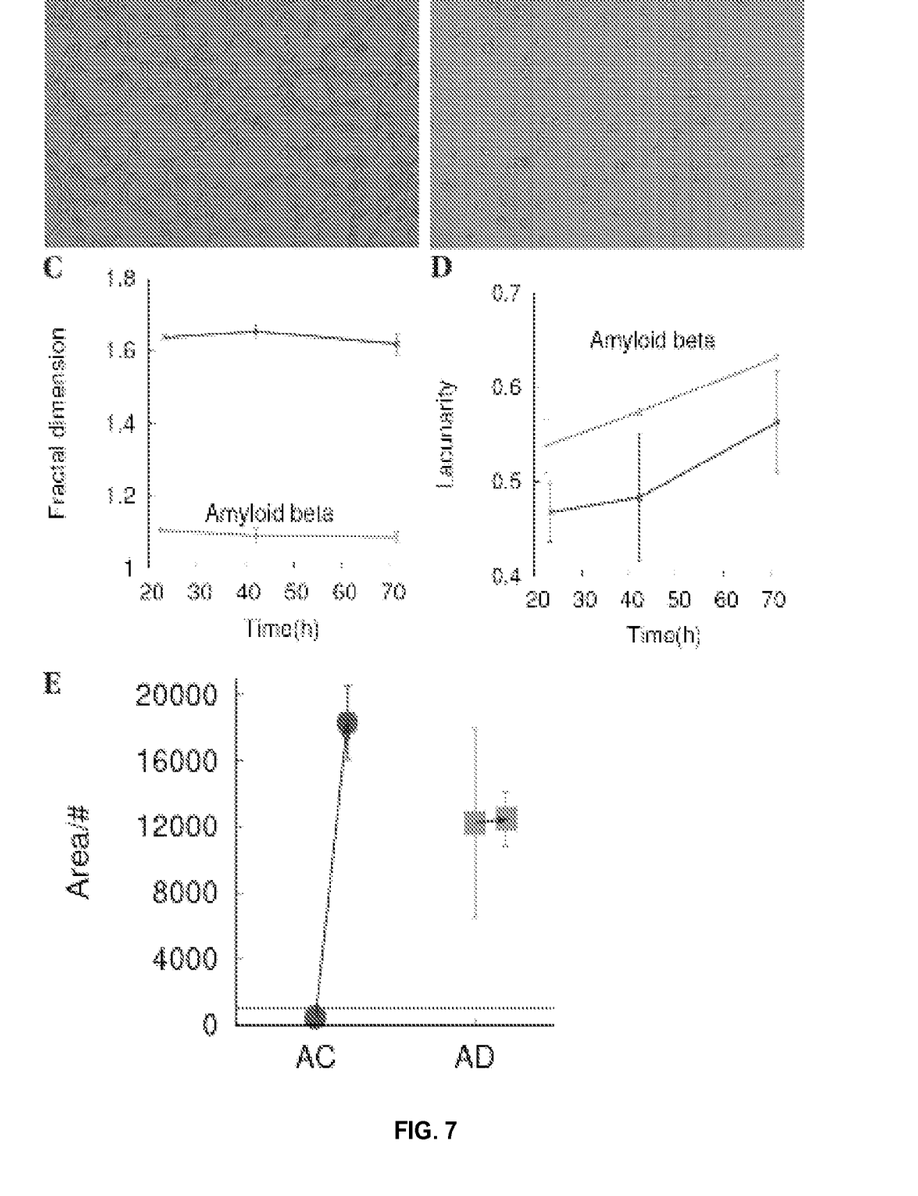
FIG. 7 shows the effect of Aβ oligomers on network formation and cellular aggregation.

AC fibroblasts treated overnight with 1 μM oligomerized Aβ changed to an AD-like phenotype when plated on Matrigel as shown in FIGS. 7A-7E. FIG. 7A shows an untreated control (AC) cell line at 2.5 hours after plating. FIG. 7B shows the same control cell line treated overnight with 1 μM oligomerized Aβ, also at 2.5 hours after plating, showing low connectivity. Impairment in network formation is further reflected through low fractal dimension and/or high lacunarity of Aβ-treated cells characteristic of AD. Fractal dimension analysis in FIG. 7C indicates that the Aβ-treated control cell line (green) is AD-like. Higher lacunarity for the Aβ-treated control cell line (green), shown in FIG. 7D, is also indicative of an AD phenotype. FIG. 7E shows increased area per number of aggregates for AC and AD cell lines 48 hours after plating, due to the 1 μM Aβ treatment in comparison to the untreated cells. Arrows in FIG. 7E point from Area/# values for the untreated AC and AD cells toward the Area/# for the Aβ-treated cells. Aβ also impaired cellular migration in AC cell lines by reducing the number of migrating cells after 48 hours, similar to AD cells (see, e.g., FIG. 6C).

Similar experiments on AD fibroblasts (n=3) showed no distinguishable effect in cellular aggregation at 48 hours, fractal dimension, or lacunarity due to Aβ treatment.

These results suggest that the large difference in area per number for Aβ-treated AC cell lines when compared with Aβ-treated AD cell lines can be useful in screening for Alzheimer's disease.

Example 3. Measure of Intercellular Communication

Skin fibroblasts were obtained from the Coriell Institute for Medical Research (Camden, N.J.). Banked fibroblasts from Alzheimer's disease (AD) patients and age match controls (AC) were maintained and cultured in T25 culture flasks with DMEM culture medium containing 10% fetal bovine serum (FBS) and 1% penicillin/streptomycin, and placed in a 5% $CO_2$ and 37° C. incubator. All flasks were regularly examined, and after 7-10 days the cultures became confluent. The total number of cell passages was not allowed to exceed 16. Cells were trypsinized, counted (cells/$mm^3$) with a cell counting chamber (Hausser Scientific), and plated in 12 well plates on a thick layer (~1.8 mm) of Matrigel. An average number of 9 counting squares was used for cell counting, with 50 cells/$mm^3$.

Five 10× images per well were used (center, up, down, left right) for quantitative image analysis. Three wells for each cell line were typically used. A cell culture microscope (Westover Digital AMID Model 2200) was used for recording the images in .png format under 10× magnification. GNU Image Manipulation (GIMP2.6) and ImageJ (1.45a) software were used for image analysis.

Images were taken 1 hour after plating the AC and AD cell lines (n=10, $p<0.03$ two tail t-test for two samples with unequal variance). The number of edges per node were manually counted as a measure of intercellular communication.

Figure 8:
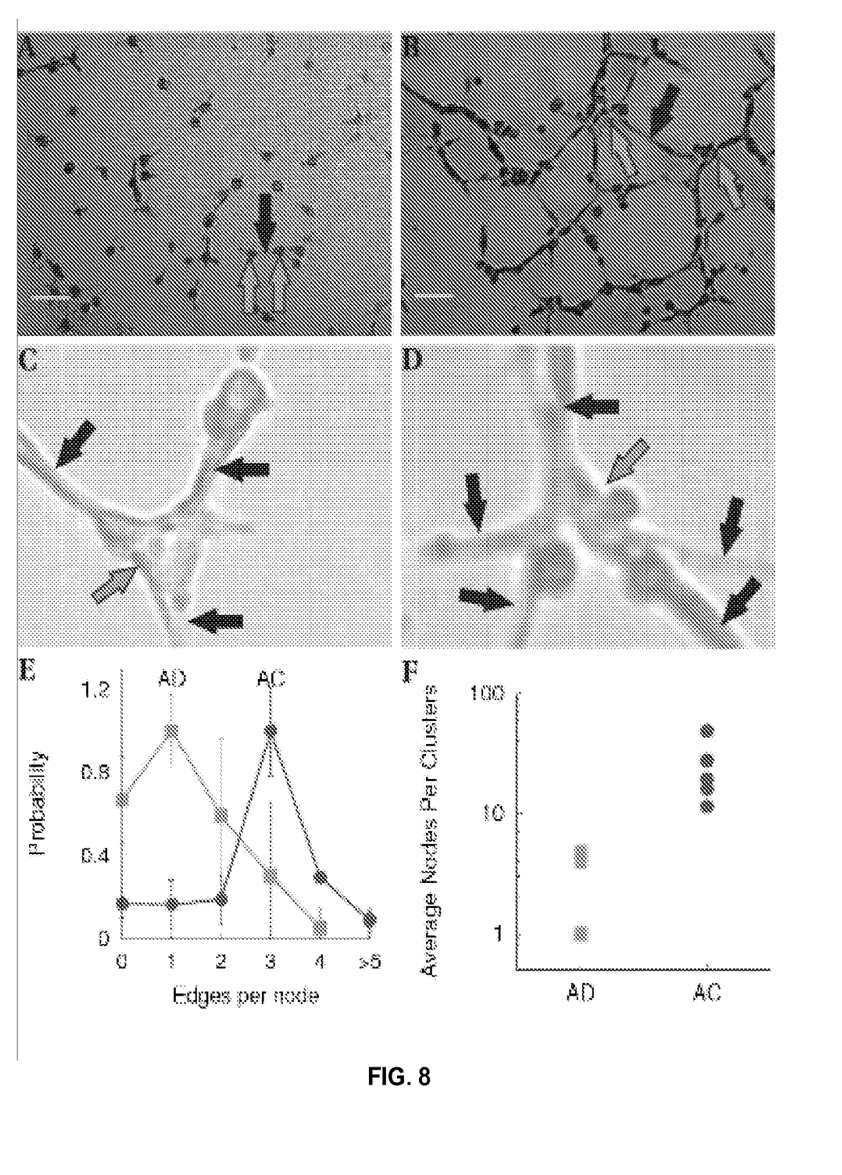
FIG. 8 illustrates determination of the number of nodes and edges per node.

FIGS. 8A and 8B show examples of AD and AC networks, respectively, comprising nodes (green arrows) and edges (blue arrows) connecting the nodes 1 hour after plating. Fibroblast cells appear as dark elliptical shapes in the images. FIG. 8C shows a node with 3 or more edges from an AC cell sample at increased magnification, and FIG. 8D shows a node with 5 edges also from an AC cell. The average number of edges per node was lower in AD cells in comparison to AC and non-ADD cells as shown in FIG. 8E, indicating that AD nodes are less connected in comparison to normal control (AC) nodes. The number of nodes per cluster of cells was also lower in the AD sample as shown in FIG. 8F, consistent with fewer edges per node.

These results suggest that intercellular communication is impaired in AD. These measures of intercellular communication could provide a rapid reading (about 1-2 hours after cell plating on a thick layer of Matrigel) and screening of patients for Alzheimer's disease.

REFERENCES

Schreml, S. et. al., *Exp. Derm.*, DO10.1111/j.1600-0625.2010.01166.x (2010).
Vierbuchen, T. et al., *Nature,* 463, 1035 (2010).
Ansel, J. C. et al., *Progress in Derm.*, 106, 198 (1996).
Geyfman, M. and B. Andersen, *J. Invest. Derm.*, 129, 1225 (2009).
Tanioka, M. et al., *J. Invest Derm.*, 129, 1225, (2009).
Selkoe, D. J., *J. Alzheimers Dis.*, 3, 75 (2001).
Hardy, J. and D. J. Selkoe, *Science,* 297, 353 (2002).
Repetto, E. et al., *J. Biol. Chem.*, 282, 31504 (2007).
Tournoy, J. et al., *Hum. Mol. Genet.*, 13, 1321 (2004).
Etcheberrigaray R. et. al., *Science,* 264, 276, (1994).

Khan, T. K. and D. L. Alkon, *P. Natl. Acad. Sci.*, 103, 13202 (2006).
Khan T. K. et. al., *Neurobiol Dis.*, 34, 332 (2009).
Etcheberrigaray, R. et. al., *P. Natl. Acad. Sci.*, 101, 11141 (2004).
Endres, K. and F. Fahrenholz, *FEBS J.*, 277, 1585 (2010).
Kozikowski, A. P. et. al., *Chem. Med. Chem.*, 4, 1095 (2009).
Aisen, P. S., *CNS Drugs*, 19, 989 (2005).
Bellucci C. et al., *Mol. Med.*, 13, 542 (2007).
Nagasaka et al., *P. Natl. Acad. Sci.*, 102, 14854 (2005).
Citron et al., *P. Natl. Acad. Sci.*, 91, 11993-7, (1994).
Johnston et al., *FEBS Lett.*, 354, 274 (1994).
Chirila, F. V. et al., *J. Physiol.*, 584, 167-190 (2007).
Watts, J. D. and S. H. Strogatz, *Nature*, 393, 440 (1998).
Albert, R. et al., *Nature*, 401, 130 (1999).
Strogatz, S. H., *Nature*, 410, 268 (2001).
Barabasi, A. L. and R. Albert, *Rev. Mod. Phys.*, 74, 47 (2002).
Fowler, J. H. and N. A. Christakis, *Brit. Med. J.*, 337, 2338 (2008).

What is claimed is:

1. A method of diagnosing Alzheimer's disease in a human subject, the method comprising:
   (a) treating a first sample of fibroblast skin cells from the subject with an amyloid beta peptide (Aβ);
   (b) separately culturing in a culture medium on an extracellular matrix (i) the resulting Aβ-treated first sample, and (ii) a second sample of fibroblast skin cells from the subject that have not been treated with Aβ, wherein the extracellular matrix comprises laminin, collagen, heparin sulfate proteoglycans, entactin/nidogen, or any combination thereof;
   (c) obtaining at least one image of each of the resulting cultured first and second samples; and
   (d) morphologically analyzing the images of the first and second samples using at least one method selected from the group consisting of determining area per number of aggregates, determining fractal dimension, and determining lacunarity,
   wherein the subject has Alzheimer's disease if there is no distinguishable difference between the results of the morphologic analyses of the first and second samples.

2. The method of claim 1, wherein step (d) comprises morphologically analyzing the images of the first and second samples by determining the area per number of aggregates.

3. The method of claim 1, wherein step (d) comprises morphologically analyzing the images of the first and second samples by determining fractal dimension.

4. The method of claim 1, wherein step (d) comprises morphologically analyzing the images of the first and second samples by determining lacunarity.

5. The method of claim 1, wherein step (d) comprises morphologically analyzing the images of the first and second samples using at least two methods selected from the group consisting of determining area per number of aggregates, determining fractal dimension, and determining lacunarity.

6. The method of claim 1, wherein step (d) comprises morphologically analyzing the images of the first and second samples by determining area per number of aggregates, determining fractal dimension, and determining lacunarity.

7. The method of claim 1, wherein the culture medium comprises a growth factor.

8. The method of claim 1, wherein step (b) comprises culturing the first and second samples for a period of from about 24 hours to about 48 hours.

* * * * *